United States Patent
Matthis et al.

(10) Patent No.: US 12,193,712 B2
(45) Date of Patent: Jan. 14, 2025

(54) BONE ANCHORING DEVICE

(71) Applicant: BIEDERMANN TECHNOLOGIES GMBH & CO. KG, Donaueschingen (DE)

(72) Inventors: Wilfried Matthis, Weisweil (DE); Martin Meer, Voehringen (DE); Lutz Biedermann, VS-Villingen (DE)

(73) Assignee: BIEDERMANN TECHNOLOGIES GMBH & CO. KG, Donaueschingen (DE)

( * ) Notice: Subject to any disclaimer, the term of this patent is extended or adjusted under 35 U.S.C. 154(b) by 50 days.

(21) Appl. No.: 17/350,633

(22) Filed: Jun. 17, 2021

(65) Prior Publication Data

US 2021/0378716 A1    Dec. 9, 2021

Related U.S. Application Data

(63) Continuation of application No. 16/416,594, filed on May 20, 2019, now Pat. No. 11,058,462, which is a
(Continued)

(30) Foreign Application Priority Data

Jan. 30, 2012    (EP) ..................................... 12153154

(51) Int. Cl.
*A61B 17/70*    (2006.01)
*A61B 17/86*    (2006.01)
*A61B 17/00*    (2006.01)

(52) U.S. Cl.
CPC ...... *A61B 17/7037* (2013.01); *A61B 17/7002* (2013.01); *A61B 17/7034* (2013.01);
(Continued)

(58) Field of Classification Search
CPC ............ A61B 17/7032; A61B 17/7034; A61B 17/7035; A61B 17/7037
See application file for complete search history.

(56) References Cited

U.S. PATENT DOCUMENTS 6,010,503 A    1/2000   Richelsoph
7,144,396 B2 *  12/2006   Shluzas .............. A61B 17/7037
                                                    606/270
(Continued)

FOREIGN PATENT DOCUMENTS

EP    2 221 012 A1    8/2010
EP    2 371 311 A1    10/2011
(Continued)

OTHER PUBLICATIONS

Extended European Search Report for European Application No. 12153154.5, European Search Report dated Jul. 3, 2012 and mailed Jul. 11, 2012 (12 pgs.).
(Continued)

*Primary Examiner* — Julianna N Harvey
(74) *Attorney, Agent, or Firm* — Lewis Roca Rothgerber Christie LLP

(57) ABSTRACT

A polyaxial bone anchoring device includes a bone anchoring element having a head and a shaft, a receiving part having a head receiving portion, a rod receiving portion, and a bore having a bore axis, and a pressure member movable in the bore and having a first surface for engaging the head, wherein the pressure member is movable to a first position where friction between the first surface and the head generates a preload on the head to maintain the shaft at a temporary angular position relative to the receiving part, and wherein the pressure member is configured to engage the receiving part to generate a holding force for holding the pressure member at the first position without a positive lock, and wherein the pressure member is movable in and out of
(Continued)

the first position by applying an axial force on the pressure member greater than the holding force.

26 Claims, 13 Drawing Sheets

Related U.S. Application Data continuation of application No. 15/436,246, filed on Feb. 17, 2017, now Pat. No. 10,335,204, which is a continuation of application No. 14/738,537, filed on Jun. 12, 2015, now Pat. No. 9,597,121, which is a continuation of application No. 13/750,988, filed on Jan. 25, 2013, now Pat. No. 9,078,705.

(60) Provisional application No. 61/592,309, filed on Jan. 30, 2012.

(52) U.S. Cl.
CPC ...... *A61B 17/7035* (2013.01); *A61B 17/8605* (2013.01); *A61B 2017/00526* (2013.01); *F04C 2270/041* (2013.01)

(56) References Cited

U.S. PATENT DOCUMENTS

| | | | |
|---|---|---|---|
| 7,604,656 | B2 | 10/2009 | Shluzas |
| 8,197,517 | B1* | 6/2012 | Lab ................... A61B 17/864 606/268 |
| 8,882,817 | B2 | 11/2014 | Jones et al. |
| 8,979,898 | B2 | 3/2015 | Ark et al. |
| 9,254,150 | B2 | 2/2016 | Biedermann et al. |
| 9,393,049 | B2 | 7/2016 | Jones et al. |
| 2004/0267264 | A1 | 12/2004 | Konieczynski et al. |
| 2005/0080420 | A1* | 4/2005 | Farris ................. A61B 17/7038 606/328 |
| 2005/0154391 | A1 | 7/2005 | Doherty et al. |
| 2005/0216003 | A1* | 9/2005 | Biedermann ...... A61B 17/7035 606/279 |
| 2005/0277928 | A1 | 12/2005 | Boschert |
| 2007/0055240 | A1 | 3/2007 | Matthis et al. |
| 2007/0118117 | A1* | 5/2007 | Altarac ............. A61B 17/7037 606/270 |
| 2007/0118123 | A1* | 5/2007 | Strausbaugh ...... A61B 17/7032 606/272 |
| 2007/0270839 | A1 | 11/2007 | Jeon et al. |
| 2008/0161859 | A1* | 7/2008 | Nilsson ................ A61B 17/704 606/266 |
| 2008/0234761 | A1* | 9/2008 | Jackson ............. A61B 17/7032 606/301 |
| 2009/0105770 | A1 | 4/2009 | Berrevoets et al. |
| 2010/0131018 | A1* | 5/2010 | Konieczynski .... A61B 17/7032 606/305 |
| 2010/0152788 | A1 | 6/2010 | Warnick |
| 2010/0160980 | A1* | 6/2010 | Walsh ................ A61B 17/7037 606/308 |
| 2010/0191293 | A1 | 7/2010 | Jackson |
| 2010/0234902 | A1* | 9/2010 | Biedermann ...... A61B 17/7037 606/305 |
| 2010/0298891 | A1 | 11/2010 | Jackson |
| 2011/0196430 | A1* | 8/2011 | Walsh ................ A61B 17/7037 606/305 |
| 2011/0213424 | A1* | 9/2011 | Biedermann ...... A61B 17/7037 606/305 |
| 2011/0251650 | A1* | 10/2011 | Biedermann ...... A61B 17/7037 606/305 |
| 2011/0282399 | A1 | 11/2011 | Jackson |
| 2012/0232598 | A1* | 9/2012 | Hestad ............... A61B 17/7037 29/446 |

FOREIGN PATENT DOCUMENTS

| | | |
|---|---|---|
| EP | 2 455 028 A1 | 5/2012 |
| EP | 2 468 198 A1 | 6/2012 |
| JP | 2010-520024 A | 6/2010 |
| JP | 2010-194309 A | 9/2010 |
| JP | 2011-206538 A | 10/2011 |
| JP | 2011-244906 A | 12/2011 |
| WO | WO 2008/112114 A1 | 9/2008 |
| WO | WO 2009/015100 A2 | 1/2009 |
| WO | WO 2009/058318 A1 | 5/2009 |
| WO | WO 2012/064360 A1 | 5/2012 |

OTHER PUBLICATIONS

Japanese Office action dated Aug. 9, 2016 for Application No. 2013-012030 and English translation (14 pages).

* cited by examiner

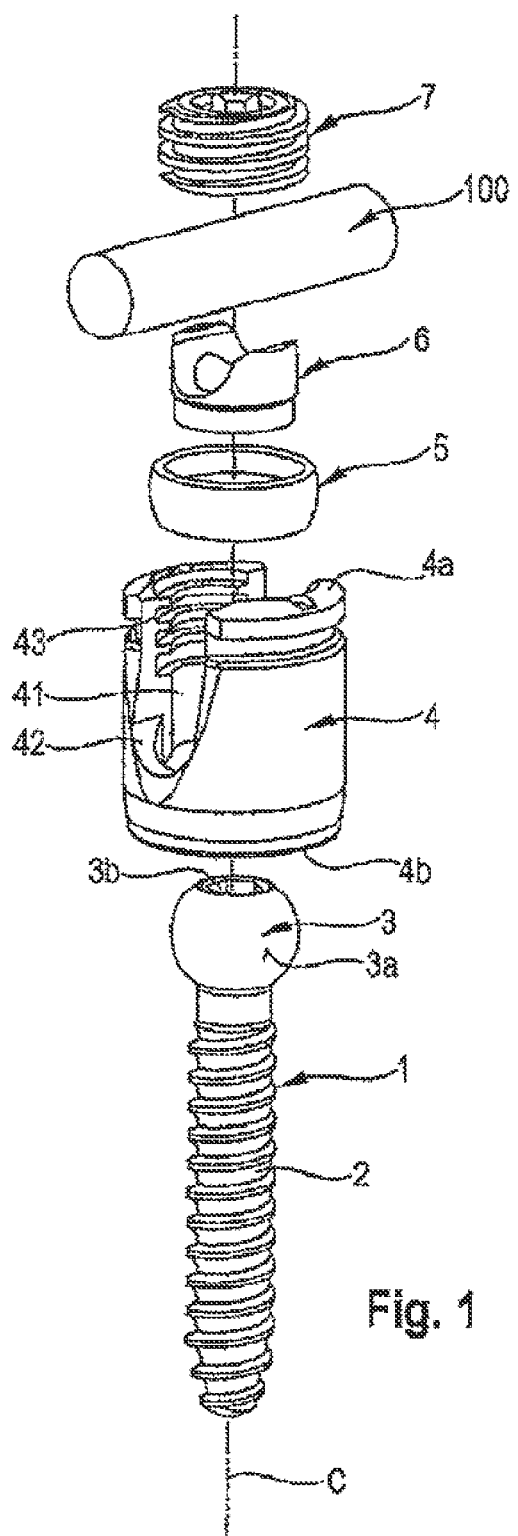
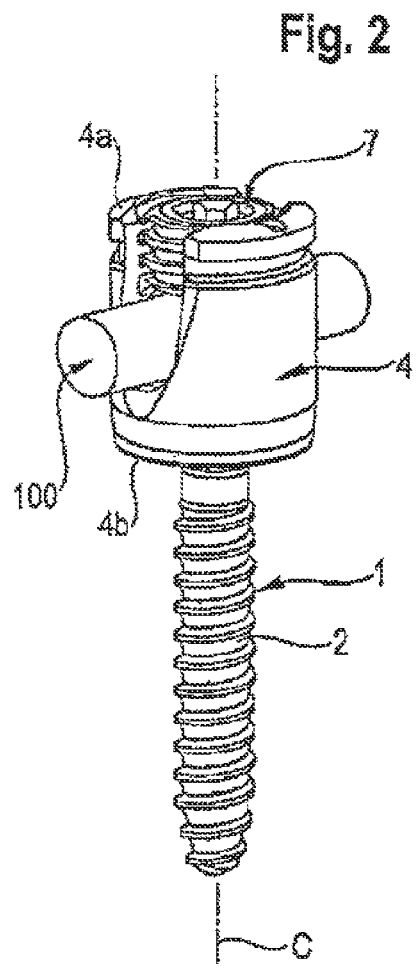
Fig. 1
Fig. 2

$F_{top} = F_{friction} + F_{preload}$

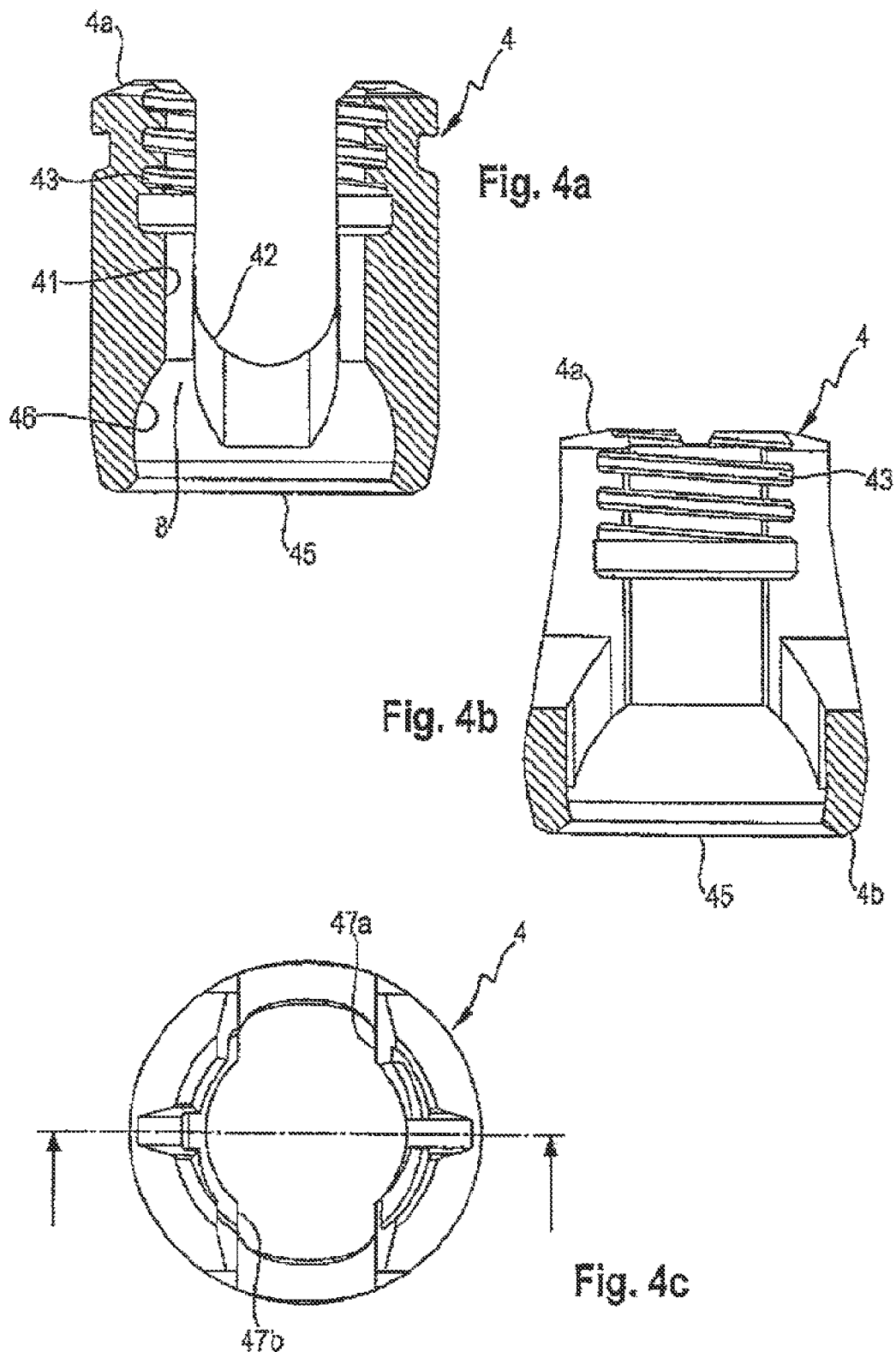

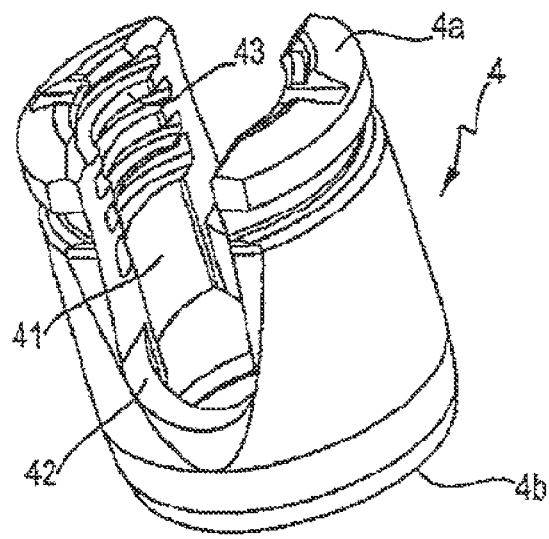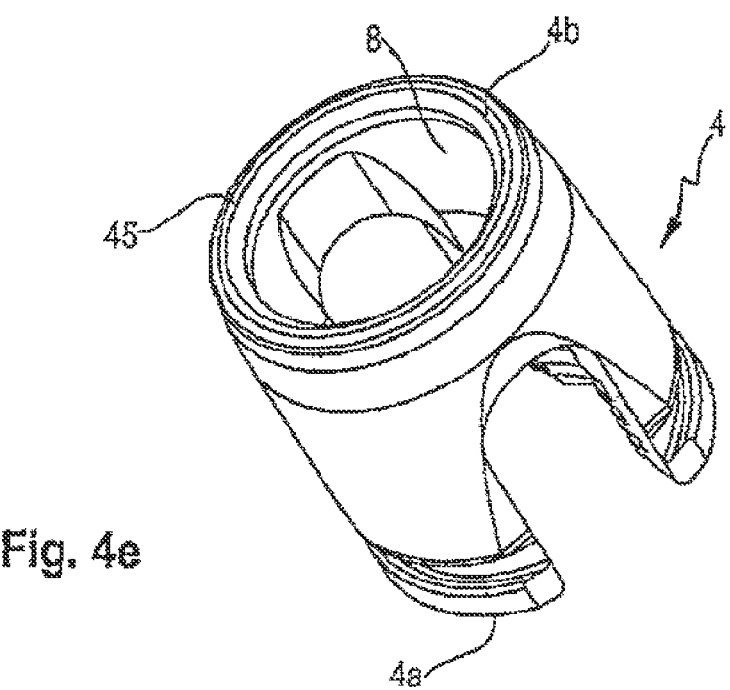

BONE ANCHORING DEVICE

CROSS-REFERENCE TO RELATED APPLICATION(S)

This application is a continuation of U.S. patent application Ser. No. 16/416,594, filed May 20, 2019, which is a continuation of U.S. patent application Ser. No. 15/436,246, filed Feb. 17, 2017, now U.S. Pat. No. 10,335,204, which is a continuation of U.S. patent application Ser. No. 14/738,537, filed Jun. 12, 2015, now U.S. Pat. No. 9,597,121, which is a continuation of U.S. patent application Ser. No. 13/750,988, filed Jan. 25, 2013, now U.S. Pat. No. 9,078,705, which claims the benefit of U.S. Provisional Patent Application Ser. No. 61/592,309, filed Jan. 30, 2012, the contents of which are hereby incorporated by reference in their entirety, and claims priority to European Patent Application No. EP 12 153 154.5, filed Jan. 30, 2012 the contents of which are hereby incorporated by reference in their entirety.

BACKGROUND

Field of Invention

The invention relates to a bone anchoring device including a bone anchoring element having a head and a shaft for anchoring in a bone, a receiving part for coupling the bone anchoring element to a rod, and a pressure member having a first surface for engaging the head and a second surface on which the rod acts. The receiving part includes an accommodation space for accommodating the head and a bore being in communication with the accommodation space, the bore having a bore axis, The pressure member is configured to assume a first position in which it exerts a preload onto the head that results from friction between the first surface and the head to enable the shaft to be maintained in a desired angular position before locking the head in the receiving part, and a second position in which the head is locked with respect to the receiving part. The first position may be achieved by moving the pressure member with a predefined force acting onto the pressure member in an axial direction, and the pressure member may be maintained or held at the first position by interaction with the receiving part, and can be released from the first position through action of another axial force.

Description of Related Art

US 2007/0118123 A1 describes a polyaxial bone anchor with increased angulation. The polyaxial bone anchor has a locking element shaped and configured to allow an anchoring member, e.g. a screw or hook, to polyaxially rotate at large angles about a central axis of the bone anchor before compression locking the anchoring member within an anchor head.

U.S. Pat. No. 7,604,656 B2 describes an apparatus including a fastener, a housing having a passage, and a spacer received in the passage and engageable with the fastener, wherein pin members retain the spacer and the fastener in the housing and wherein an end portion of the pin members has a tapered surface by which the spacer is urged axially toward the fastener when the pin member is inserted through the housing. The pin members also apply an axial force to the spacer to prevent relative movement between the spacer and the housing when the rod is disengaged from the spacer and the spacer engages the fastener. The pin members hold the spacer in frictional engagement with the fastener.

SUMMARY

Although the polyaxial bone anchoring devices described above provide for an enlarged angulation in a desired orientation, there is still a need for an improved polyaxial bone anchoring device in terms of simplicity of design and handling of the device.

It is an object of embodiments of the invention to provide an improved polyaxial bone anchoring device.

With a polyaxial bone anchoring device according to embodiments of the invention, a temporary clamping of a head of a bone anchoring element, with a more exact predetermined force in a desired angular position with respect to a receiving part, without finally locking the head, can be achieved. In this condition, a pressure member exerts a preload force onto the head in which the head is not locked, but is prevented or restricted from freely pivoting by friction. The preload is achieved by applying an axial force on the pressure member. The preload is then maintained by a radial force which acts on the pressure member, and frictionally holds the pressure member in position with respect to the receiving part. When the head is temporarily clamped, the alignment of the receiving part with respect to a rod and the insertion of the rod, is more readily facilitated, in particular, in situations in which a multitude of bone anchors are to be connected to the rod.

A mechanism to frictionally maintain the position of the head before locking is free from any spring members or similar parts or portions. The polyaxial bone anchoring device has few parts, and is of a simple design. According to an embodiment, for achieving the preload onto the head, no further parts are required due to an interference fit connection. Referring to the interference fit connection, radial forces, for example, arranged at a 90° angle to a longitudinal axis of the receiving part, result from elastic deformation of the material of the part or parts. The bone anchoring device can be manufactured easily and cost-effectively. Furthermore, existing receiving parts can be used without having to redesign their shape. Only the pressure members have to be adapted or modified, so that an interference fit between an outer diameter of the pressure member and an inner diameter of the receiving part can be achieved.

An amount of preload exerted onto the head by the pressure member can be exactly predefined in a simple manner during assembly by adjusting the externally applied axial force. The preload onto the head generated in this way is reproducible. The polyaxial bone anchoring device according to embodiments of the invention can be provided to the surgeon in a pre-assembled manner, in which the pressure member is axially and rotationally fixed by friction in the receiving part to such an extent that it can not fall out or be rotated out of its aligned position. This allows for safer handling by the surgeon. Furthermore, by mounting the pressure member by means of a tool with a predetermined force, a repeatable friction fit, or interference fit connection can be achieved.

According to a further aspect of embodiments of the present invention, the polyaxial bone anchoring device provides for an enlarged pivot angulation of the bone screw by attaching a sleeve-like insert while equally providing high efficiency of fixation. A pivot angle of the bone anchoring element relative to the receiving part may be equal to or greater than 45° measured from a straight position. This renders the bone anchoring device particularly suitable for, for example, applications of lateral mass fixation, for example, in the cervical spine. The locking mechanism for locking the bone anchoring element and the sleeve-like insert piece provides for a high clamping force on a small surface. Therefore, the locking mechanism may be more efficient.

BRIEF DESCRIPTION OF THE DRAWINGS

Further features and advantages of the invention will become apparent from the description of embodiments by means of the accompanying drawings. In the drawings:

FIG. 1 shows a perspective exploded view of a polyaxial bone anchoring device with a spinal rod according to a first embodiment;

FIG. 2 shows a perspective view of the bone anchoring device of FIG. 1 in an assembled state;

FIG. 3b shows an enlarged portion of the cross-sectional front view of the bone anchoring device of FIG. 3a;

FIG. 4a shows a cross-sectional front view (i.e., rotated from FIG. 4a by 90°) of a receiving part according to a first embodiment;

FIG. 4b shows a cross-sectional side view of the receiving part according to the first embodiment;

FIG. 4c shows a top view of the receiving part according to the first embodiment;

FIG. 4d shows a perspective top view of the receiving part according to the first embodiment;

FIG. 4e shows a perspective bottom view of the receiving part according to the first embodiment;

FIG. 8b shows an enlarged portion of the cross-sectional view of the bone anchoring device of to FIG. 8a;

FIG. 11b shows an enlarged portion of the cross-sectional view of the bone anchoring device of FIG. 11a;

DETAILED DESCRIPTION

Figure 3A:
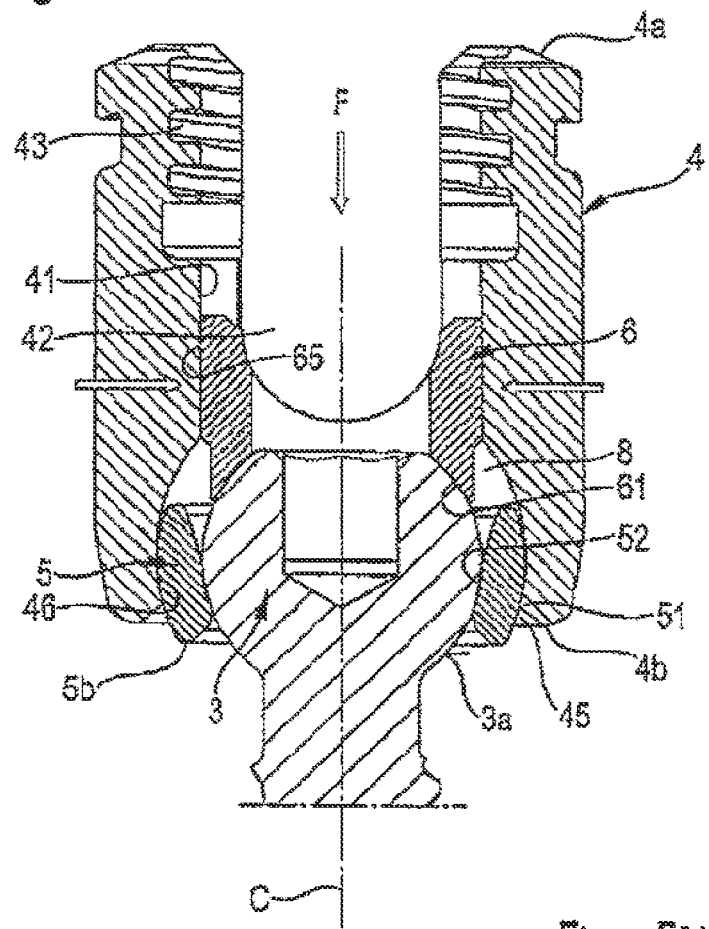
FIG. 3a shows a cross-sectional front view of the bone anchoring device of FIGS. 1 and 2 in the assembled state without the rod and without a fixation screw.

As shown in FIGS. 1 to 3b, a polyaxial bone anchoring device according to a first embodiment includes a bone anchoring element 1 in the form of a bone screw having a threaded shaft 2 and a head 3. The head 3 typically has a spherically-shaped outer surface portion 3a and a recess 3b at its free end for engagement with a tool, e.g., a driver. The head 3 can be held in a receiving part 4 that couples the bone anchoring element 1 to a stabilization rod 100. In an assembled state, in the receiving part 4, a sleeve-like insert piece 5 providing a seat for the head 3 of the bone anchoring element 1 and a pressure member 6 for exerting pressure onto the head 3 can be arranged. Furthermore, a fixation element in the form of a fixation screw 7 is provided for securing and fixing the rod 100 in the receiving part 4. In some embodiments, a bone anchoring device without the sleeve-like insert piece 5 is also possible. In those cases, the seat for the head 3 may be provided in the receiving part directly.

As can be seen from FIGS. 1 to 4e the receiving part 4 has a top end 4a and a bottom end 4b, a central axis C, and a coaxial bore 41 extending from the top end 4a in the direction of the bottom end 4b. Adjacent to the top end 4a, a U-shaped recess 42 is provided that forms a channel for receiving the rod 100. By means of the U-shaped recess 42, two free legs are formed, which are provided with an internal thread 43 for cooperating with an outer thread of the fixation screw 7 in an assembled state (see, e.g., FIG. 2).

The coaxial bore 41 opens into an accommodation space 8 provided in a lower region of the receiving part 4. The accommodation space 8 has a lower opening 45 at the bottom end 4b of the receiving part 4. The accommodation space 8 further includes a seat portion 46 near the bottom end 4b of the receiving part 4, in which the sleeve-like insert piece 5 can be seated. The seat portion 46 has a spherical shape in order to provide a socket portion for a ball and socket joint formed between the sleeve-insert piece 5 and the receiving part 4. It should be noted that the seat portion 46 can alternatively be tapered or can have another shape that can be used to realize a ball and socket joint. A smallest inner diameter at the lower opening 45 is smaller than a largest inner diameter of the accommodation space 8. It shall be noted that an inner diameter of the coaxial bore 41 does not need to be constant between the top end 4a and the accommodation space 8. The bore 41 may have different portions with different diameters.

In order to allow the sleeve-like insert piece 5 to be introduced from the top end 4a, two opposed recesses 47a, 47b (see, e.g., FIGS. 4c-4e) are provided in the inner wall of the coaxial bore 41 and/or the accommodation space 8. The recesses 47a, 47b may be aligned with the U-shaped recess 42. They may extend from the bottom of the U-shaped recess 42 into the accommodation space 8. The size of the recesses 47a, 47b is such that the sleeve-like insert piece 5 can be introduced from the top end in a 90° tilted or vertical position, where a width of the recesses 47a, 47b is greater than a height of the sleeve-like insert piece 5 in its axial direction. The recesses 47a, 47b extend into the accommodation space 8 to such an extent that inserting of the sleeve-like insert piece 5 into the seat 46 in such a tilted position is facilitated.

The pressure member 6 is shown in particular in FIGS. 5a to 5e. The pressure member 6 is substantially cylindrical, with an outer diameter that allows the pressure member 6 to be moved within the coaxial bore 41 and the accommodation space 8, for example, by means of a tool. However, in some embodiments an outer diameter of the pressure member 6 is slightly larger than an inner diameter of the coaxial bore 41 to achieve an interference fit or press fit connection between the inner surface of the coaxial bore 41 and an outer surface 65 of the pressure member 6. It is also possible that in some embodiments, only parts of the mentioned surfaces form the interference fit. The pressure member 6 has an upper end 6a and a lower end 6b. Adjacent its lower end 6b, the pressure member 6 has a recess 61 with a spherical shape that matches the shape of the outer spherical surface portion 3a of the head 3. At the upper end 6a, the pressure member 6 has a cylindrical recess 63 for receiving the rod 100 therein. Furthermore, the pressure member 6 has a coaxial bore 64 for allowing access to the screw head 3 with a tool when the device is in an assembled state. By the coaxial bore 64 and the cylindrical recess 63, two legs are formed facing the top end 4a. The coaxial bore 64 is also configured to allow a portion of the head 3 to extend therethrough when the bone anchoring element 1 is in a pivoted condition.

The sleeve-like insert piece 5 is shown in particular in FIGS. 6a-6d. The sleeve-like insert piece 5 has an upper end 5a and a lower end 5b. Between the upper end 5a and the lower end 5b, the sleeve-like insert piece 5 has a spherical-shaped outer surface portion 51. A largest outer diameter of the sleeve-like insert piece 5 is greater than the smallest inner diameter of the lower opening 45 of the receiving part 4. Hence, the sleeve-like insert piece 5 cannot escape through the lower opening 45 when it is seated in the receiving part 4. The dimension of the outer spherical surface portion 51 corresponds to the spherical-shaped seat portion 46 of the receiving part 4 in such a way that the sleeve-like insert piece 5 can pivot and rotate in the receiving part 4 when it is seated in the seat portion 46. When the sleeve-like insert piece 5 rests in the seat portion 46 such that its central axis 5c is coaxial with a central axis C of the receiving part 4, the lower end 5b may project out of the lower opening 45. When the sleeve-like insert piece 5 is pivoted in the receiving part 4, at least a portion of the lower end 5b projects out of the lower opening 45.

The sleeve-like insert piece 5 is hollow and has a central inner portion 52 that is spherically-shaped with a radius corresponding to a radius of the spherically-shaped outer surface portion 3a of the head 3 of the bone anchoring element 1. A lower end of the central portion 52 forms a shoulder 53. The inner diameter of the shoulder 53 is smaller than a largest outer diameter of the spherical head 3 so that the head 3 can rotate and pivot in the central spherical portion 52 of the sleeve-like insert piece 5, similar to a ball and socket joint. Between the shoulder 53 and the lower end 5b, a tapered portion 54 is provided that tapers outwards to allow angulation of the bone anchoring element 1 until the shaft 2 comes into contact with the tapered portion 54 of the lower end 5b. Between the spherical central portion 52 and the upper end 5a, a tapered portion 55 is provided, which tapers outwards. An inner diameter of the tapered portion 55 and of the transition between the tapered portion 55 and the spherical central portion 52 is greater than the largest outer diameter of the head 3, so that the head 3 can be inserted from the upper end 5a into the sleeve-like insert piece 5. At the upper end 5a, a chamfered portion 56 may be provided that may serve as a stop for the pressure member 6.

Respective center points of the spherical central portion 52 and of the outer spherical portion 51 may be offset in such a way that the center point of the inner central spherical portion 52 is shifted in a direction towards the bottom end 4b (i.e., closer to lower end 5b than the center point of the outer spherical portion 51). By means of this, a range of angulation for the bone anchoring element 1 can be further increased. A height of the sleeve-like insert piece 5 in an axial direction is less than a height of the head 3 in an axial direction, such that when the head 3 is inserted into the sleeve-like insert piece 5, a portion of the spherical outer surface 3a of the head 3 projects from the upper end 5a of the sleeve-like insert piece 5, for example, as can be seen from FIG. 3a.

The sleeve-like insert piece 5 and the anchoring element 1 are independently pivotable when the shaft 2 of the anchoring element 1 and the lower end 5b of the sleeve-like insert piece 5 are out of contact. When the shaft 2 of the bone anchoring element 1 is pivoted and engages the lower end 5b of the sleeve-like insert piece 5, further pivoting of the bone anchoring element 1 in a direction corresponding to the contact causes the sleeve-like insert piece 5 to pivot together with the bone anchoring element 1. When the pressure member 6 is in contact with the head 3, there may be a gap between the pressure member 6 and the sleeve-like insert piece 5.

Figure 3B:
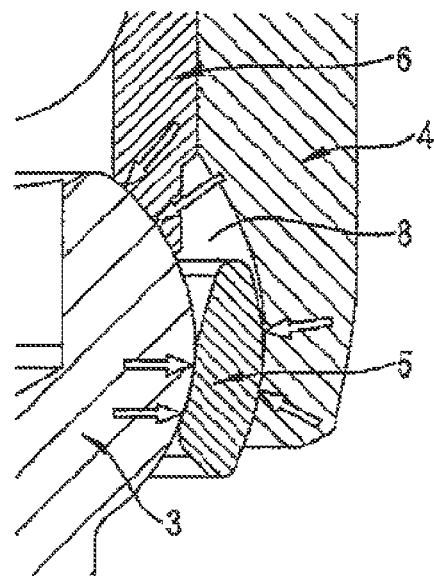
Figure 5A:
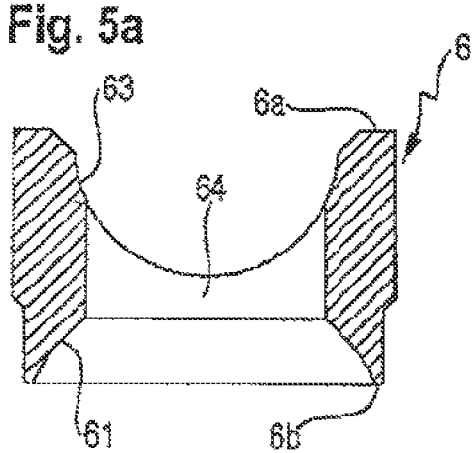
FIG. 5a shows a cross-sectional front view of a pressure member according to a first embodiment.
Figure 5B:
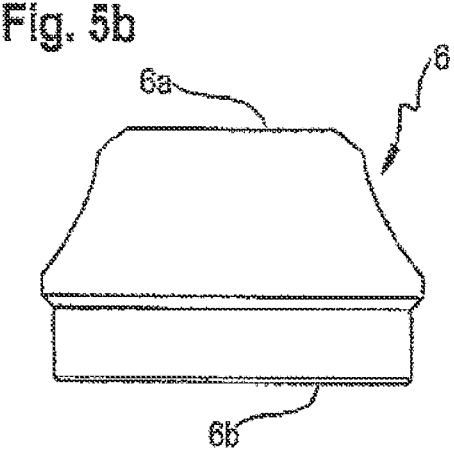
FIG. 5b shows a side view of the pressure member according to the first embodiment.
Figure 5C:
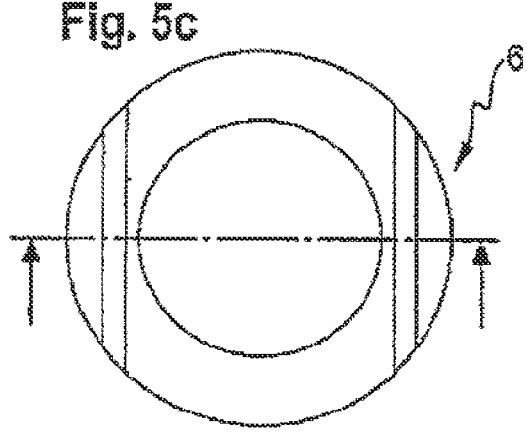
FIG. 5c shows a top view of the pressure member according to the first embodiment.
Figure 5D:
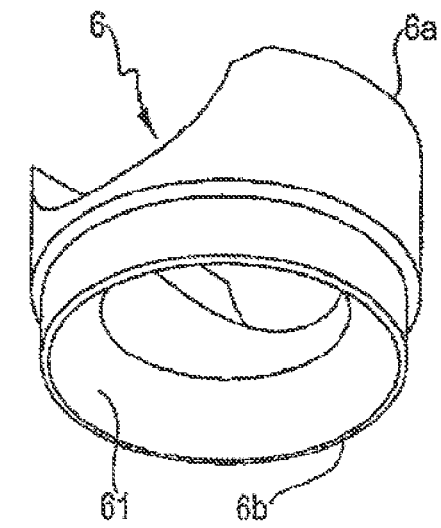
FIG. 5d shows a perspective bottom view of the pressure member according to the first embodiment.
Figure 5E:
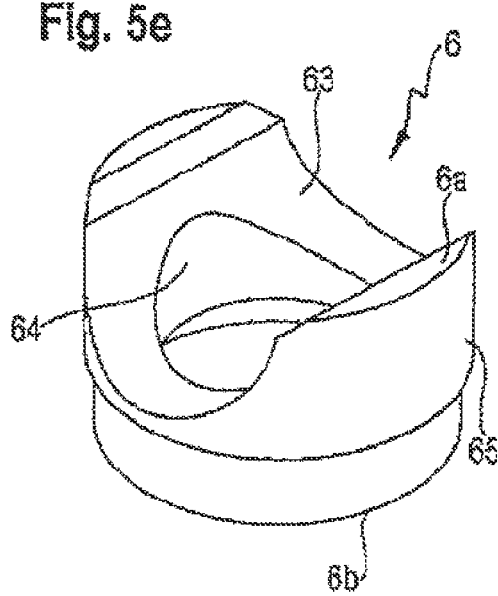
FIG. 5e shows a perspective top view of the pressure member according to the first embodiment.
Figure 6A:
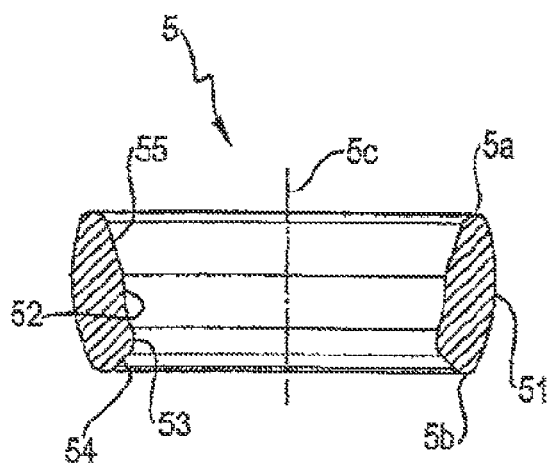
FIG. 6a shows a cross-sectional front view of a sleeve-like insert.
Figure 6B:
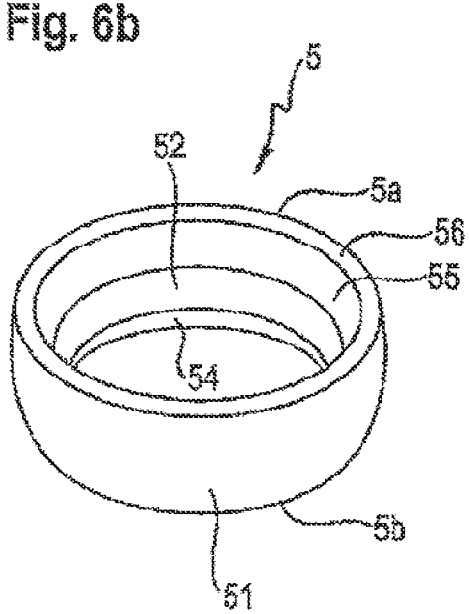
FIG. 6b shows a perspective top view of the sleeve-like insert.
Figure 6C:
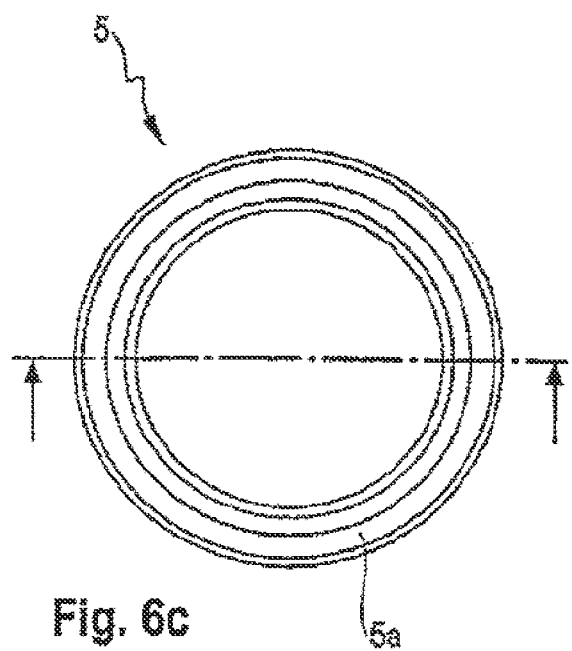
FIG. 6c shows a top view of the sleeve-like insert.
Figure 6D:
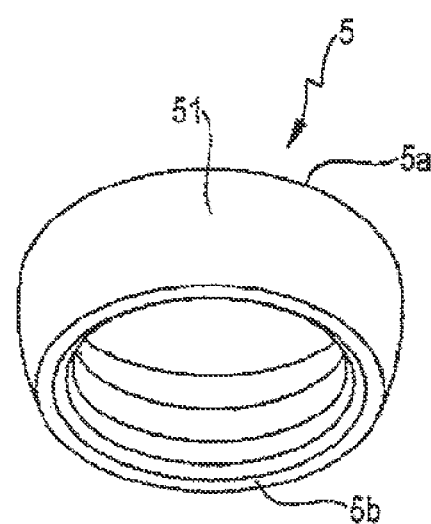
FIG. 6d shows a perspective bottom view of the sleeve-like insert.

As indicated by arrows in FIGS. 3a, 3b, a force F which is provided from above in the figures is divided between frictional resistance (indicated by the two horizontal arrows in FIG. 3a) and a preload force (indicated by the small arrows in FIG. 3b), which holds the head with respect to the receiving part 4 in a desired angular orientation by friction. The frictional resistance results from the interference fit connection between the pressure member 6 and the receiving part 4, where the outer diameter of at least one portion of the pressure member 6 is slightly larger than the inner diameter of a corresponding portion of the receiving part 4. The preload force acting on the head 4 leads to a small elastic preload of the whole system.

Figure 7A:
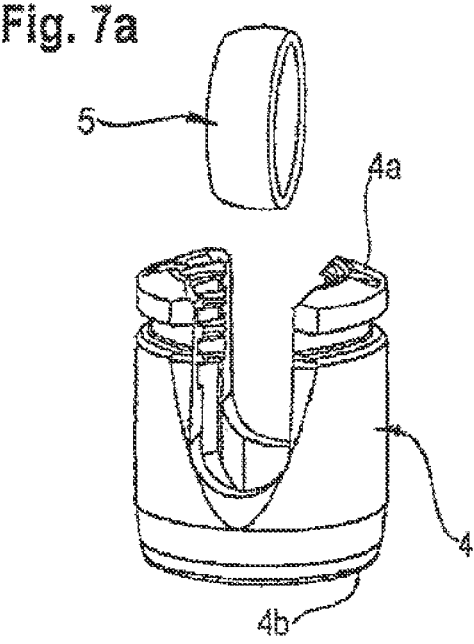
FIGS. 7a to 7h show steps of assembling the sleeve-like insert, the receiving part, the bone anchoring element and the pressure member, according to one embodiment.
Figure 7B:
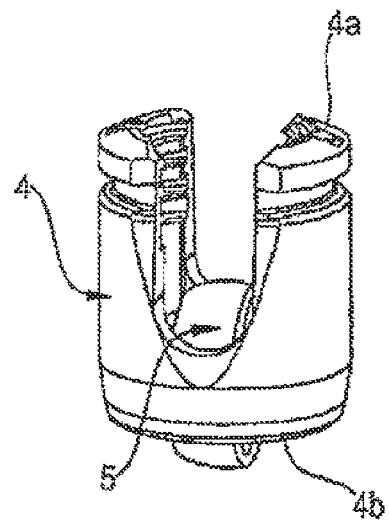
Figure 7C:
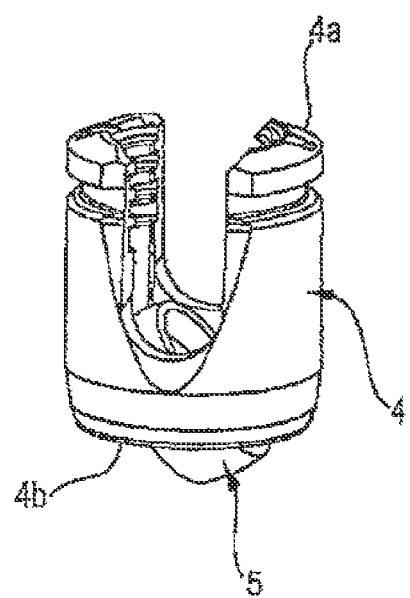
Figure 7D:
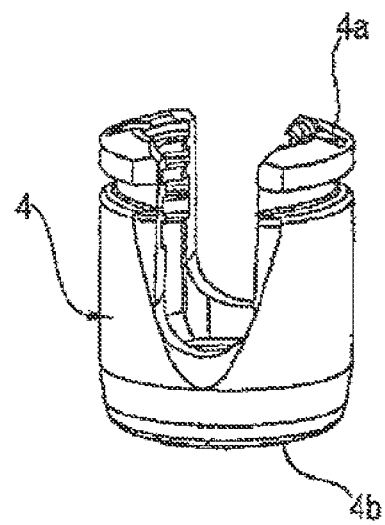

The steps of pre-assembling the bone anchoring device according to the first embodiment are shown with respect to FIGS. 7a to 7h. The bone anchoring device according to the first embodiment may be pre-assembled in such a way that, first the sleeve-like insert piece 5 is tilted by 90° and inserted into the receiving part 4 at the position of the U-shaped recess 42, as can be seen in FIGS. 7a and 7b. As shown in FIG. 7b the sleeve-like insert piece 5 is moved downwards into the accommodation space 8. Since the largest outer diameter of the sleeve-like insert piece 5 is larger than the smallest inner diameter the lower opening 45 of the receiving part 4, the sleeve-like insert piece 5 cannot escape through the lower edge of the lower opening 45. Then, as shown in FIGS. 7c and 7d the sleeve-like insert piece 5 is tilted so that it is finally seated in the seat portion 46 of the receiving part 4, as shown in FIG. 7d.

Figure 7E:
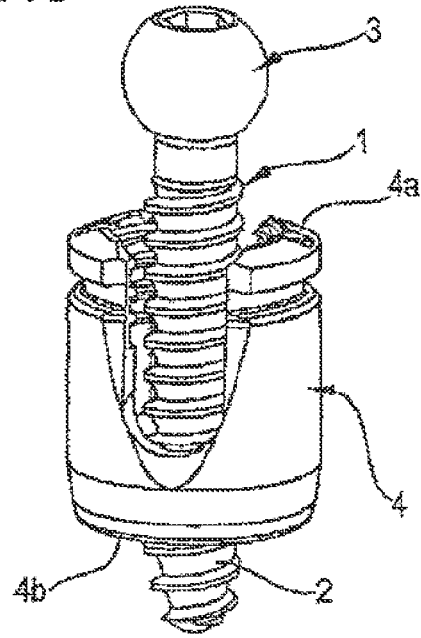
Figure 7F:
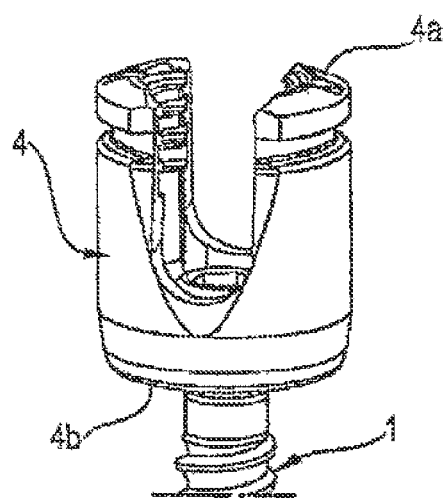
Figure 7G:
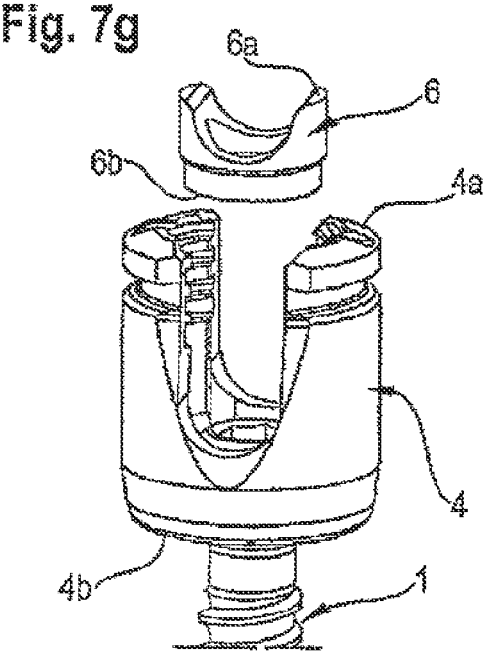
Figure 7H:
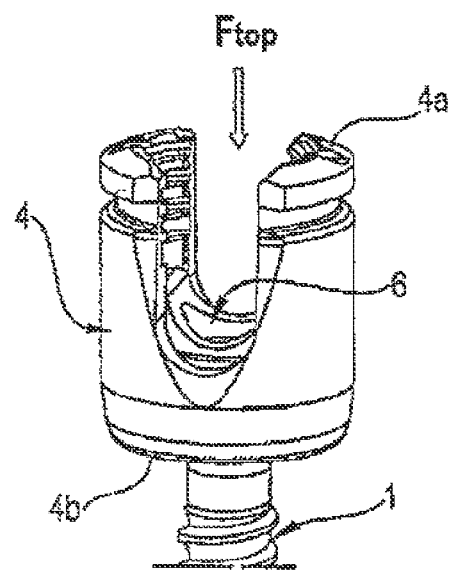

Thereafter, the bone anchoring element 1 is inserted, for example, from the top end 4a of the receiving part 4 until the outer surface portion 3a of the head 3 engages the seat portion 52 of the sleeve-like insert piece 5, as can be seen in FIGS. 7e and 7f. Then, the pressure member 6 is inserted from the top end 4a, as can be seen in FIG. 7g, and a predefined force is applied from the top, as indicated by the arrow in FIG. 7h. The pressure member 6 is arranged in an aligned position, in which the cylindrical recess 63 is aligned with the U-shaped recess 42 of the receiving part 4 for receiving the rod 100. Dependent on the degree of the interference fit connection, it may be necessary to use a tool for pushing down the pressure member 6 into the receiving part 4. The predefined force from above may be generated manually or by a tool, for example, and may be constant and/or force-controlled or path-controlled.

The bone anchoring device as a whole or in parts is made of a bio-compatible material, such as a bio-compatible metal, for example titanium, stainless steel, of a bio-compatible alloy, such as nitinol, or of a bio-compatible plastic material, such as, for example, polyetheretherketone (PEEK).

FIGS. 8a to 10 show a second embodiment of a bone anchoring device. Parts and portions which are the same or similar to those of the first embodiment are designated with the same reference numerals, and the descriptions thereof may not be repeated. The bone anchoring device according to the second embodiment differs from the bone anchoring device of the first embodiment by the construction of the outer surface 65' of the pressure member 6' and of the corresponding inner surface of the coaxial bore 41' of the receiving part 4'. All other parts are identical or similar to those of the first embodiment.

Figure 8A:
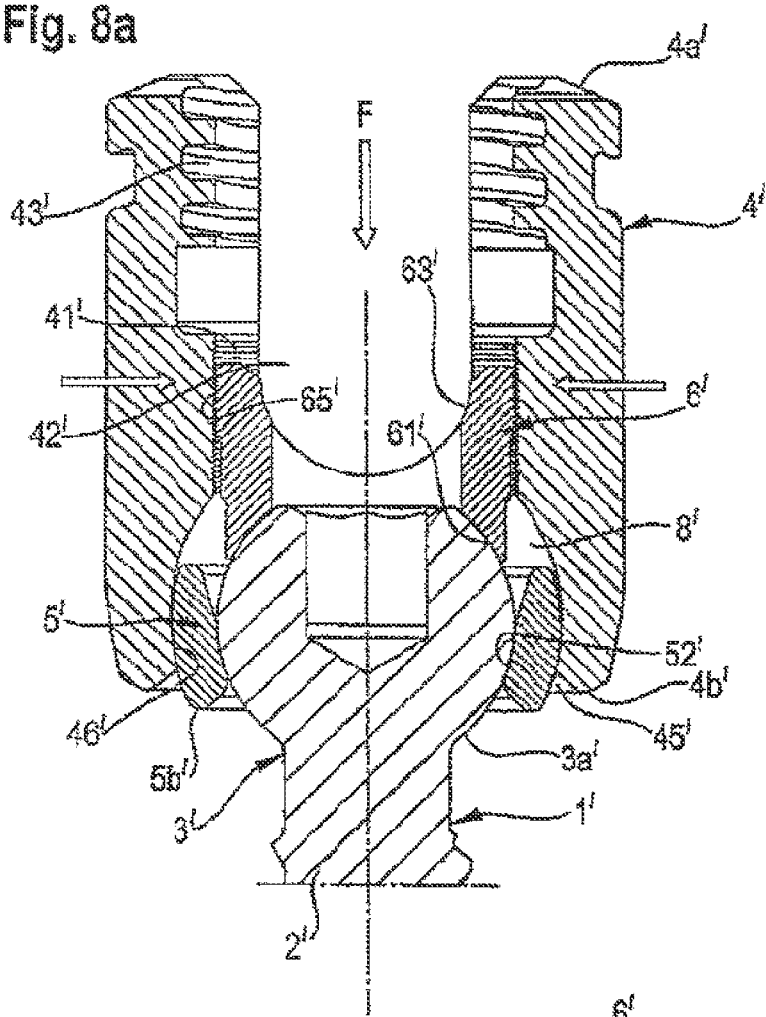
FIG. 8a shows a cross-sectional view of a bone anchoring device in an assembled state, without a rod or a fixation screw, according to a second embodiment, the cross-section taken perpendicular to an axis of a rod channel of the device.
Figure 8B:
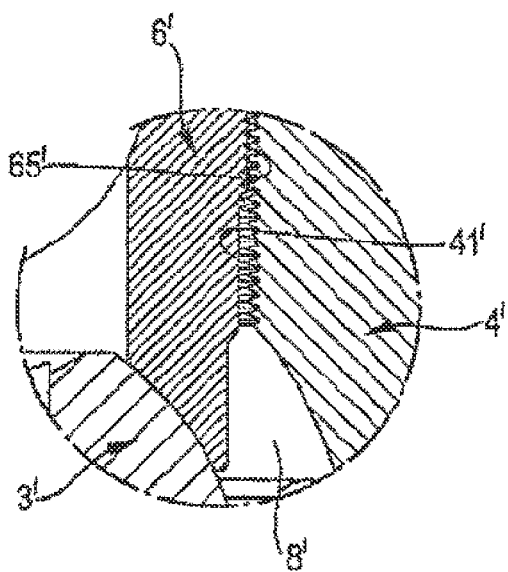
Figure 9:
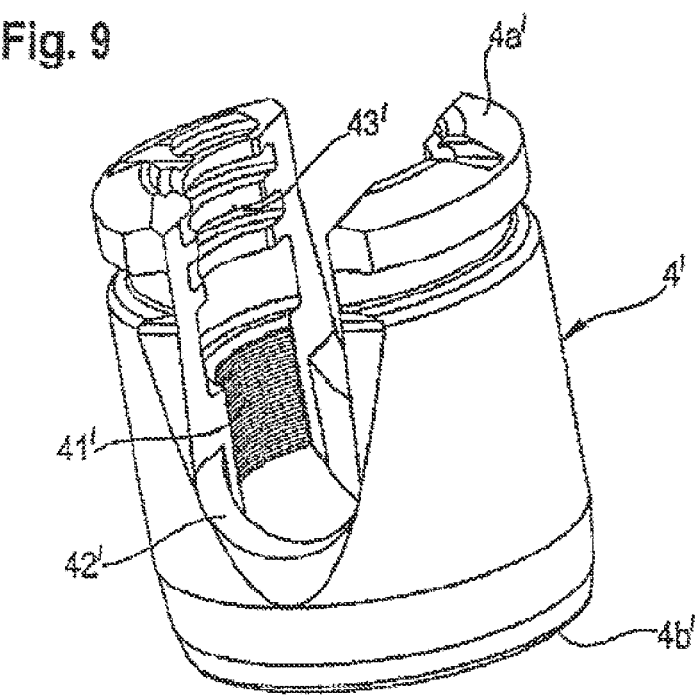
FIG. 9 shows a perspective view of a receiving part according to a second embodiment.
Figure 10:
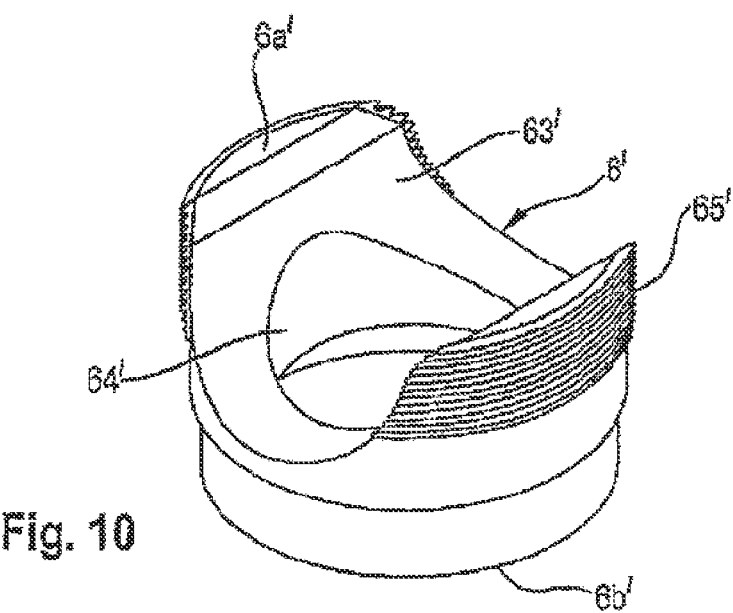
FIG. 10 shows a perspective view of a pressure member according to a second embodiment.
Figure 11A:
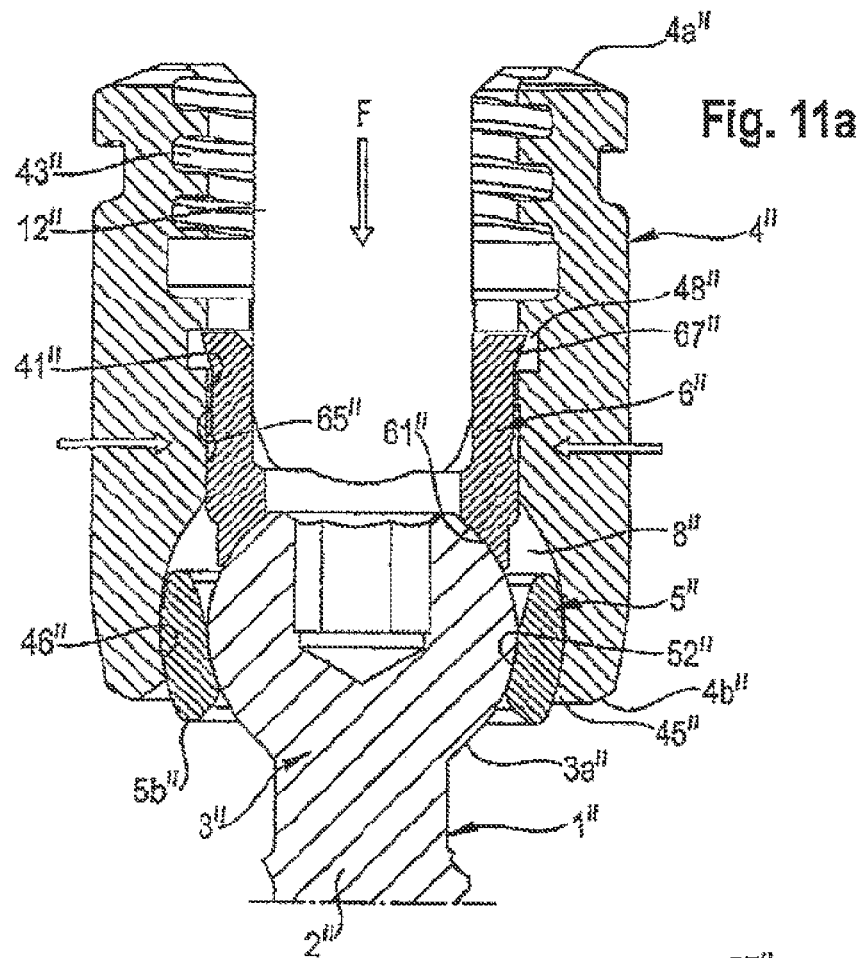
FIG. 11a shows a cross-sectional view of a bone anchoring device in an assembled state, without a rod or a fixation screw, according to a third embodiment, the cross-section taken perpendicular to an axis of a rod channel of the device.
Figure 11B:
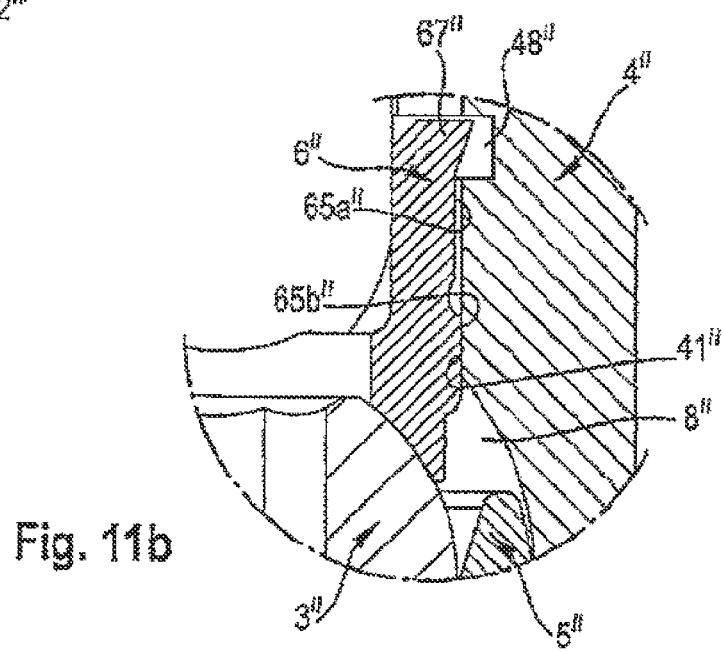
Figure 12:
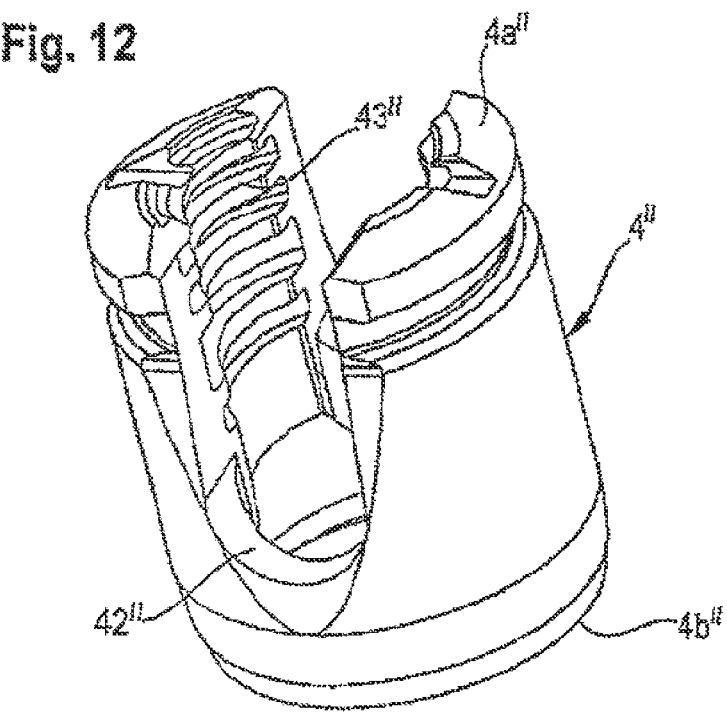
FIG. 12 shows a perspective view of a receiving part according to a third embodiment.
Figure 13:
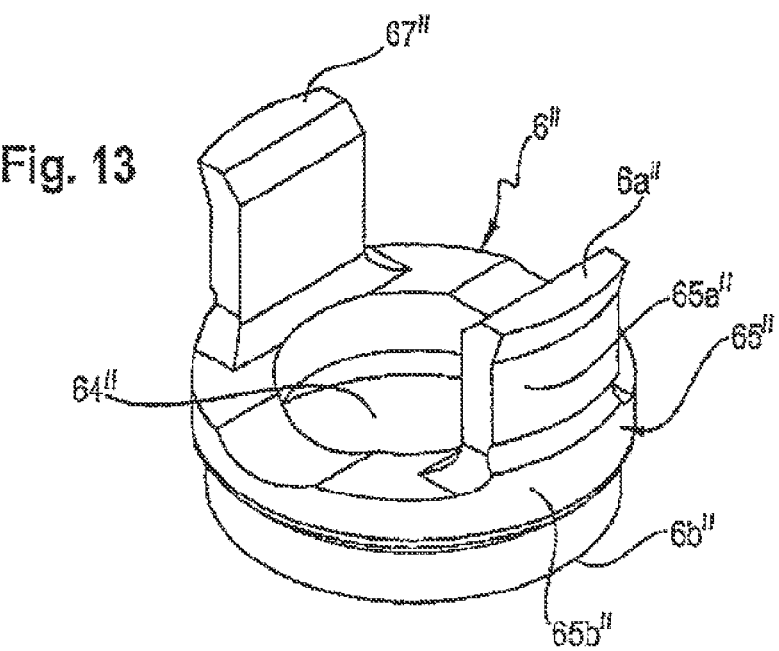
FIG. 13 shows a perspective view of a pressure member according to a third embodiment.

As can be seen, especially in FIG. 8b, the inner surface of the coaxial bore 41' is structured, for example, is roughened or fluted or grooved or ridged. The outer surface 65' of the pressure member 6' may also be structured, for example, may also be roughened or fluted or grooved or ridged. The surface interaction of the two surfaces prevents or restricts the pressure member 6' from inadvertently moving backwards towards the first end 4a'. Therefore, a holding function of the interference fit connection is further increased. It is also possible that only one of the surfaces is structured as described above.

FIGS. 11a to 13 show a third embodiment of a bone anchoring device. Parts and portions which are the same or similar to those of the first embodiment are designated with same reference numerals, and the descriptions thereof may not be repeated. The bone anchoring device according to the third embodiment differs from the bone anchoring device of the first embodiment by the construction of the pressure member 6" and the corresponding portions of the receiving part 4". All other parts are identical or similar to those of the first embodiment.

Referring to the outer surface 65" of the pressure member 6", which has an upper portion 65a" and a lower portion 65b" with slightly different outer diameters, an interference fit in this embodiment may only be present at the lower portion 65b" of the outer surface of the pressure member 6", which contacts the inner surface of the coaxial bore 41" of the receiving part 4". Therefore, in this embodiment, only the diameter of the lower portion 65b" may be slightly larger than an inner diameter of the corresponding portion of the coaxial bore 41". The diameter of the upper portion 65a" may be the same or smaller than the diameter of the coaxial bore 41". The upper portion 65a" may further include two projections 67" at the free ends of the legs of the pressure member 6", where the projections 67" extend radially outwards and can latch into an annular groove 48" provided in the coaxial bore 41" of the receiving part 4" when the pressure member 6" is inserted into the receiving part 4". Due to the larger outer diameter of the projections 67" with respect to the inner diameter of the rest of the coaxial bore 41", the legs of the pressure member 6" may be compressed towards each other and elastically expand when the projections 67" snap into the grooves 48".

Pre-assembling of the bone anchoring device according to the second and third embodiments corresponds or are similar to the pre-assembling according to the first embodiment.

Figure 14:
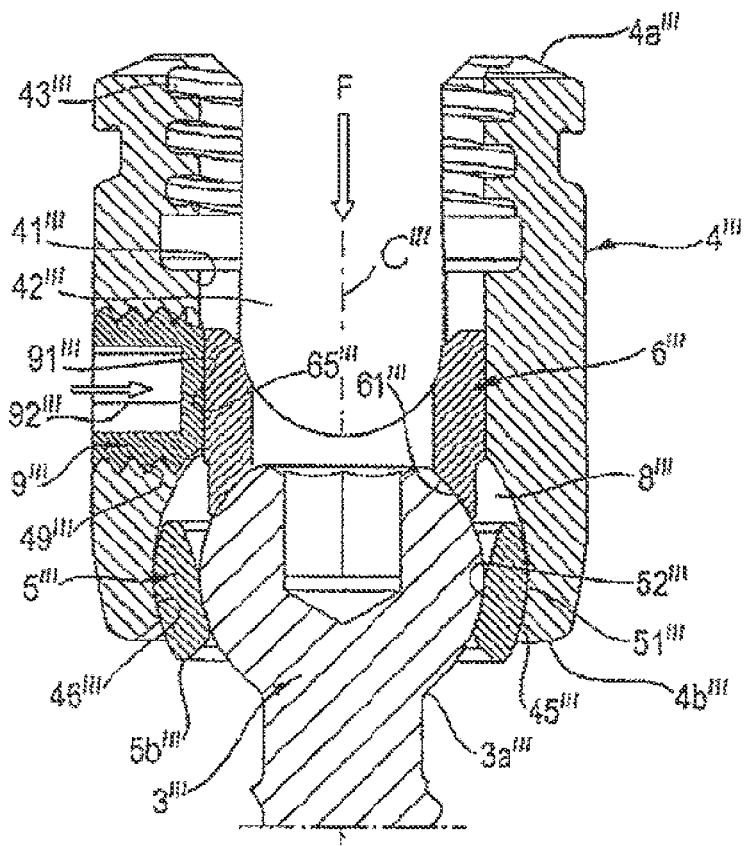
FIG. 14 shows a cross-sectional view of a bone anchoring device in an assembled state, without a rod or a fixation screw, according to a fourth embodiment, the cross-section taken perpendicular to an axis of a rod channel of the device.

FIG. 14 shows a fourth embodiment of a bone anchoring device. Parts and portions which are the same or similar to those of the first embodiment are designated with same reference numerals, and the descriptions thereof may not be repeated. The bone anchoring device according to the fourth embodiment differs from the bone anchoring device according to the first embodiment in that there is no interference fit connection between the receiving part 4''' and the pressure member 6''', where an outer diameter of at least one portion of the pressure member 6''' is equal to or smaller than an inner diameter of the corresponding portions of the receiving part 4'''. Instead, a set screw 9''' is provided which is screwed into a through bore 49''' located in one leg of the receiving part 4''' during assembly, for fixing the pressure member 6''' relative to the receiving part 4'''. The set screw 9''' has an engagement portion 92''' for engagement with a tool and a flat bottom side 91''' for cooperating with the outer surface 65''' of the pressure member 6'''. All other parts are identical or similar to those of the first embodiment.

The first steps of pre-assembling the bone anchoring device according to the fourth embodiment correspond or are similar to the pre-assembling according to the first embodiment. A predefined force is applied on the pressure member 6''' from above to define or determine a preload force acting on the head 3'''. After that, the pressure member 6''' is frictionally fixed by screwing in the set screw 9'''. The set screw 9''' only acts radially, or perpendicular to an axis C''', onto the outer surface 65''' of the pressure member 6''', and the pressure member 6'''' is thereby held in place. Therefore, the preload force acing on the head 3'''' is maintained.

Figure 15:
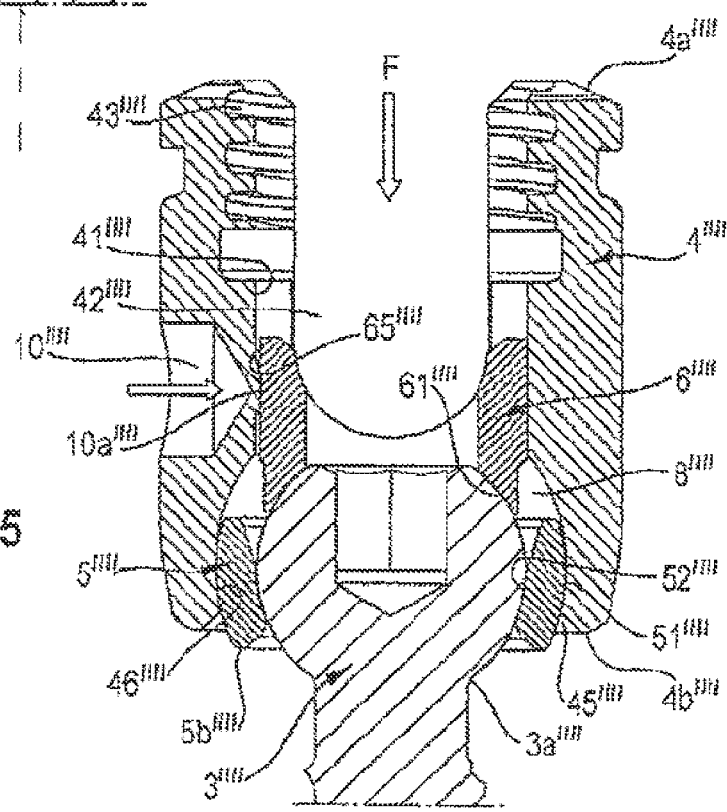
FIG. 15 shows a cross-sectional view of a bone anchoring device in an assembled state, without a rod or a fixation screw according to a fifth embodiment, the cross-section taken perpendicular to an axis of a rod channel of the device.

FIG. 15 shows a fifth embodiment of a bone anchoring device. Parts and portions which are the same or similar to those of the first embodiment are designated with same reference numerals, and the descriptions thereof may not be repeated. The bone anchoring device according to the fifth embodiment differs from the bone anchoring device according to the first embodiment in that there is no interference fit connection between the receiving part 4'''' and the pressure member 6'''', where an outer diameter of at least one portion of the pressure member 6'''' is equal to or smaller than an inner diameter of the corresponding portions of the receiving part 4''''. A crimping blind hole 10'''' is provided, which is located in one leg of the receiving part 4''''. All other parts are identical or similar to those of the first embodiment.

The first steps of pre-assembling the bone anchoring device according to the fifth embodiment correspond or are similar to the pre-assembling according to the first embodiment. A predefined force is applied on the pressure member 6'''' from above to define or determine a preload force acting on the head 3''''. After that, the pressure member 6'''' can be frictionally fixed by crimping, for example, by means of a crimping tool. Here, a deformable portion 10a'''' of the receiving part 4'''' adjacent to the crimping blind hole 10'''' can be deformed, and the deformed material radially exerts a pressure force onto the outer surface 65'''' of the pressure member 6'''', by which the pressure member 6'''' is held in place. Therefore, the preload force acting on the head 3'''' can be maintained.

Further modifications of the embodiments described are also conceivable. For example, for the bone anchoring element, various different kinds of anchoring elements can be used and combined with the receiving parts. Such bone anchoring elements may be, for example, screws of different lengths, screws with different diameters, cannulated screws, screws with different thread forms, nails, hooks, etc. In some embodiments, the head and the shaft of the anchoring element may also be separate parts that are connectable to each other.

Further modifications of the receiving part may include, for example, a recess for the rod that is inclined or open to the side, instead of a U-shaped recess which is perpendicular to a central axis of the receiving part. Other kinds of locking devices, including outer nuts, outer caps, bayonet locking devices, or various other devices, may also be utilized. In embodiments of the invention, an inner surface portion of the pressure member that contacts the head may not necessarily be spherical-shaped, and can have any other shape suitable for exerting pressure onto the head of the bone anchoring element.

In some embodiments, it is also possible to use a two-part locking device for separately fixing the rod and the head of the bone anchoring element relative to the receiving part.

In some embodiments, it is also possible that the pressure member can be prevented from rotation by additional crimping.

It shall further be noted that portions or features of the various different embodiments described above can be combined with one another.

While the present invention has been described in connection with certain exemplary embodiments, it is to be understood that the invention is not limited to the disclosed embodiments, but is instead intended to cover various modifications and equivalent arrangements included within the spirit and scope of the appended claims, and equivalents thereof.

What is claimed is:

1. A polyaxial bone anchoring device comprising:
   a bone anchoring element having a head and a shaft for anchoring to a bone;
   a receiving part for coupling the bone anchoring element to a rod, the receiving part having a first end and a second end below the first end, a central axis extending between the first and second ends, a head receiving portion at the second end defining an accommodation space for accommodating the head, and a rod receiving portion at the first end defining a recess for receiving the rod; and
   a separate pressure member comprising a first surface for engaging the head, a second surface for engaging the rod, and an outer surface, wherein the first, second, and outer surfaces are connected to one another;
   wherein when the head of the bone anchoring element is in the receiving part, the pressure member is movable from the first end of the receiving part to a first position where friction between the head and the first surface of the pressure member generates a preload on the head to maintain the shaft at a temporary angular position relative to the receiving part, wherein the head is configured to be substantially free from any preload until the first surface engages the head, while a holding force directed towards the central axis is configured to start acting on a portion of the outer surface of the pressure member that is located at a first radial distance from the central axis before the first surface engages the head;
   wherein when the pressure member is at the first position, the holding force directed towards the central axis is configured to continue acting on the portion of the outer surface of the pressure member at the first radial distance from the central axis to hold the pressure member at the first position to maintain the preload on the head; and
   wherein the pressure member is movable from the first position to a second position different from the first position where the angular position of the shaft is locked relative to the receiving part.

2. The polyaxial bone anchoring device of claim 1, wherein the pressure member is held at the first position by a radial force that generates friction between the pressure member and an inner surface of the receiving part.

3. The polyaxial bone anchoring device of claim 1, wherein when a sufficient axial force is applied to the pressure member, the pressure member is movable from the first position to a third position above the first position where the preload on the head is released and the head is configured to be substantially free from any downward forces applied thereupon.

4. The polyaxial bone anchoring device of claim 1, wherein the receiving part defines a seat that is directly engageable with the head to hold the head.

5. The polyaxial bone anchoring device of claim 1, further comprising a separate insert that is positionable in a recess formed in a side wall of the receiving part to contribute to the holding force for holding the pressure member at the first position.

6. The polyaxial bone anchoring device of claim 1, further comprising a separate insert that is positionable in a recess formed in a side wall of the receiving part to contribute to the generating of the preload on the head.

7. The polyaxial bone anchoring device of claim 1, wherein a longitudinal axis of the bone anchoring element is configured to form a maximum pivot angle with the central axis of the receiving part that is at least 45°.

8. The polyaxial bone anchoring device of claim 1, wherein the bone anchoring element is insertable into the receiving part from the first end of the receiving part.

9. A polyaxial bone anchoring device comprising:
   a bone anchoring element having a head and a shaft for anchoring to a bone;
   a receiving part for coupling the bone anchoring element to a rod, the receiving part having a first end and a second end below the first end, a central axis extending between the first and second ends, a rod receiving portion at the first end defining a recess for receiving the rod, and a head receiving portion at the second end defining a seat that is directly engageable with the head to hold the head, wherein the head of the bone anchoring element is insertable from the first end of the receiving part into the seat, and wherein the seat is configured to hold the head without contacting any portion of the head above a greatest diameter of the head measured in a direction perpendicular to the central axis; and
   a separate pressure member comprising a first surface for engaging the head, a second surface for engaging the rod, and an outer surface, wherein the first, second, and outer surfaces are connected to one another;

wherein when the head of the bone anchoring element is held in the seat, the pressure member is movable from the first end of the receiving part to a first position where friction between the head and the first surface of the pressure member generates a preload on the head to maintain the shaft at a temporary angular position relative to the receiving part, wherein an engaging surface of the bone anchoring device positioned at a first radial distance from the central axis is configured to engage and exert a holding force directed towards the central axis on the pressure member before the pressure member reaches the first position;

wherein when the pressure member is at the first position, the engaging surface is configured to remain at the first radial distance from the central axis while continuing to exert the holding force directed towards the central axis on the pressure member to hold the pressure member at the first position to maintain the preload on the head; and wherein the pressure member is movable from the first position to a second position different from the first position where the angular position of the shaft is locked relative to the receiving part.

10. The polyaxial bone anchoring device of claim 9, wherein an inner surface of the receiving part comprises the engaging surface, and wherein the pressure member is held at the first position by a radial force that generates friction between the pressure member and the inner surface of the receiving part.

11. The polyaxial bone anchoring device of claim 9, wherein the head is configured to be freely separable from the seat when the head and the pressure member are in the receiving part.

12. The polyaxial bone anchoring device of claim 9, further comprising a separate insert that is positionable in a recess formed in a side wall of the receiving part, wherein the separate insert comprises the engaging surface and contributes to the holding force for holding the pressure member at the first position.

13. The polyaxial bone anchoring device of claim 9, further comprising a separate insert that is positionable in a recess formed in a side wall of the receiving part to contribute to the generating of the preload on the head.

14. The polyaxial bone anchoring device of claim 9, wherein the seat extends continuously and uninterruptedly around substantially an entire circumference of the head.

15. The polyaxial bone anchoring device of claim 9, wherein the seat is positioned at or near the second end of the receiving part.

16. The polyaxial bone anchoring device of claim 9, wherein the seat is formed on an insert piece that is movable relative to other portions of the receiving part.

17. The polyaxial bone anchoring device of claim 9, wherein a longitudinal axis of the bone anchoring element is configured to form a maximum pivot angle with the central axis of the receiving part that is at least 45°.

18. A polyaxial bone anchoring device comprising:
a bone anchoring element having a head and a shaft for anchoring to a bone;
a receiving part for coupling the bone anchoring element to a rod, the receiving part having a first end and a second end below the first end, a central axis extending between the first and second ends, a head receiving portion at the second end defining an accommodation space for accommodating the head, and a rod receiving portion at the first end defining a recess for receiving the rod; and
a separate pressure member comprising a first surface for engaging the head, a second surface for engaging the rod, and an outer surface, wherein the first, second, and outer surfaces are connected to one another;
wherein when the head is in the receiving part, corresponding engagement structures that are formed on the outer surface of the pressure member and on an inner surface of the receiving part are configured to engage one another while the pressure member is advanced from the first end of the receiving part and prior to reaching a first position where friction between the head and the first surface of the pressure member generates a preload on the head to maintain the shaft at a temporary angular position relative to the receiving part;
wherein the corresponding engagement structures restrict the pressure member from moving out of the first position towards the first end of the receiving part; and
wherein the pressure member is movable from the first position to a second position different from the first position where the angular position of the shaft is locked relative to the receiving part.

19. The polyaxial bone anchoring device of claim 18, wherein the pressure member is held at the first position by a radial force that generates friction between the pressure member and the inner surface of the receiving part.

20. The polyaxial bone anchoring device of claim 18, wherein when the head is in the receiving part, the head is movable downward to directly engage a seat and movable upward to disengage from the seat.

21. The polyaxial bone anchoring device of claim 18, wherein the head is configured to be freely separable from a seat for the head when the head and the pressure member are in the receiving part.

22. The polyaxial bone anchoring device of claim 18, wherein the bone anchoring element is insertable into the receiving part from the first end of the receiving part.

23. The polyaxial bone anchoring device of claim 18, where the head is prevented from being inserted from the second end of the receiving part into the accommodation space.

24. The polyaxial bone anchoring device of claim 18, wherein a longitudinal axis of the bone anchoring element is configured to form a maximum pivot angle with the central axis of the receiving part that is at least 45°.

25. The polyaxial bone anchoring device of claim 18, wherein the corresponding engagement structures comprise grooves and/or ridges.

26. The polyaxial bone anchoring device of claim 18, wherein the receiving part defines a seat that is directly engageable with the head to hold the head.

* * * * *